United States Patent
Takei

(10) Patent No.: US 12,270,879 B2
(45) Date of Patent: Apr. 8, 2025

(54) MAGNETIC RESONANCE IMAGING DEVICE, VASCULAR IMAGE GENERATION METHOD, AND RECORDING MEDIUM

(71) Applicant: GE Precision Healthcare LLC, Wauwatosa, WI (US)

(72) Inventor: Naoyuki Takei, Tokyo (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 116 days.

(21) Appl. No.: 18/073,394

(22) Filed: Dec. 1, 2022

(65) Prior Publication Data
US 2023/0194638 A1  Jun. 22, 2023

(30) Foreign Application Priority Data
Dec. 21, 2021 (JP) .................. 2021-206856

(51) Int. Cl.
*G01R 33/48* (2006.01)
*A61B 5/055* (2006.01)
*G01R 33/385* (2006.01)

(52) U.S. Cl.
CPC .......... *G01R 33/4828* (2013.01); *A61B 5/055* (2013.01); *G01R 33/385* (2013.01)

(58) Field of Classification Search
CPC .... G01R 33/4828; G01R 33/385; A61B 5/055
See application file for complete search history.

(56) References Cited

U.S. PATENT DOCUMENTS

| 2012/0197104 A1* | 8/2012 | Posse | G01R 33/4838 600/410 |
| 2016/0327623 A1* | 11/2016 | Nakai | G01R 33/5607 |
| 2016/0360979 A1* | 12/2016 | Lindner | A61B 5/0044 |

(Continued)

FOREIGN PATENT DOCUMENTS

| JP | 2020163023 A | 10/2020 |
| JP | 2021510568 A | 4/2021 |
| WO | 2015115187 A1 | 8/2015 |

OTHER PUBLICATIONS

Irie et al., "Accelerated acquisition of carotid MR angiography using 3D gradient-echo imaging with two-point Dixon", Neuroradiology vol. 62, 10 (2020): 1345-1349, 5 pages.

(Continued)

*Primary Examiner* — Sean A Frith
(74) *Attorney, Agent, or Firm* — Andrus Intellectual Property Law, LLP

(57) ABSTRACT

A system for acquiring an image in which deterioration of vascular signals due to improved water-fat swap is provided. The system includes a magnetic resonance imaging device, which receives an out-of-phase signal and in-phase signal from an imaging site including a blood vessel. The system also includes a processor that processes a digital signal including data representing the out-of-phase signal and in-phase signal. The processor executes an operation including: generating a water image Wa based on the digital signal; and adding a signal intensity $|I_{in}|$ of the out-of-phase signal and a signal intensity of the in-phase signal to the water image Wa to generate a vascular image representing the blood vessel.

20 Claims, 9 Drawing Sheets

(56) References Cited

U.S. PATENT DOCUMENTS

| | | | | |
|---|---|---|---|---|
| 2017/0227620 A1* | 8/2017 | Wakai | .............. | G01R 33/56308 |
| 2017/0307699 A1* | 10/2017 | Rodgers | ............. | G01R 33/3875 |
| 2020/0386838 A1* | 12/2020 | Miyazaki | ........... | G01R 33/5607 |
| 2021/0045634 A1 | 2/2021 | Pang | | |

OTHER PUBLICATIONS

JP Application 2021-206856 filed Dec. 21, 2021—First Office Action issued Sep. 14, 2022; 6 pages.

Koktzoglou et al., "High spatial resolution whole-neck MR angiography using thin-slab stack-of-stars quiescent interval slice-selective acquisition", Magn Reson Med. 2020; 84: 3316-3324, 9 pages.

Leiner et al., "Subtractionless first-pass single contrast medium dose peripheral MR angiography using two-point Dixon fat suppression", Eur Radiol 23, 2228-2235 (2013), 8 pages.

Namiki et al., "3D time of flight MRA using radial-based gradient echo pulse sequence with modified DIXON of the aortic arch bifurcation", Netherlands. #1617, ISMRM 2021, 2 pages.

Nezafat et al., "Coronary MR angiography at 3T: fat suppression versus water-fat separation." Magma (New York, N.Y.) vol. 29,5 (2016): 733-8, 6 pages.

Yoneyama et al., "Free-breathing non-contrast-enhanced flow-independent MR angiography using magnetization-prepared 3D non-balanced dual-echo Dixon method: A feasibility study at 3 Tesla," Magnetic resonance imaging vol. 63 (2019): 137-146, 10 pages.

\* cited by examiner

MAGNETIC RESONANCE IMAGING DEVICE, VASCULAR IMAGE GENERATION METHOD, AND RECORDING MEDIUM

CROSS REFERENCE

The present application claims priority and benefit of Japanese Patent Application No. 2021-206856 filed on Dec. 21, 2021, which is incorporated herein by reference in its entirety.

TECHNICAL FIELD

The present invention relates to a magnetic resonance imaging device that generates a vascular image, a vascular image generation method of generating a vascular image, and a recording medium storing a command for generating a vascular image.

BACKGROUND

Magnetic Resonance Imaging (MRI) devices are known as medical devices that non-invasively capture images of the inside of a patient's body. MRI devices do not irradiate the patient with X-rays, but rather apply a magnetic field to the patient to collect image data. Therefore, MRI devices can collect image data without exposing patients to radiation, and therefore are widely used in hospitals and other medical facilities as highly safe medical devices.

SUMMARY

MRI devices can acquire various types of MR images, and therefore are very important in diagnosing patients. For example, if a patient's blood vessels are to be imaged, magnetic resonance angiography (MRA) can be used to obtain vascular images of the patient. A well-known technique for acquiring vascular images is water-fat separation MRA using a single slab Dixon method (for example, see Non-Patent Documents 1 and 2). Also known is a water-fat separation technique using a multi-slab Dixon method. Water-fat separation MRA using the Dixon method is a promising technique that provides favorable fat separation, is robust to B0 and B1 inhomogeneity, and is resistant to motion artifacts. In the Dixon method, an MRA blood signal is visualized using a water image calculated from the difference in chemical shifts between water and fat. However, if a B0 heterogeneity appears in an anatomical region (for example, at a boundary portion between tissue and air) with a sudden phase change, a "water-fat swap" occurs, where the signal of the supposedly water image becomes the signal of the fat image and the signal of the supposedly fat image signal becomes the signal of the water image and may result in a false separation. This results in a lower blood signal in the water image and a higher signal in the fat image. Therefore, it may be difficult to obtain high-quality vascular images because the vascular signal is buried in a background signal.

Therefore, it is desirable to acquire an image in which deterioration of vascular signals due to water-fat swap is improved.

A first aspect of the present invention is a magnetic resonance imaging device that receives a plurality of MR signals with different echo times from an imaging site including a blood vessel. The magnetic resonance imaging device includes one or a plurality of processors that process a digital signal including data representing the plurality of MR signals. The one or plurality of processors execute an operation including: generating a water image based on the digital signal; and combining the water image and signal intensity of each MR signal to generate a vascular image representing the blood vessel.

A second aspect of the present invention is a vascular image generation method, comprising: receiving a plurality of MR signals with different echo times from an imaging site including a blood vessel. The method further includes generating a water image based on a digital signal containing data representing the plurality of MR signals; and combining the water image and a signal intensity of each MR signal to generate a vascular image representing the blood vessel.

A third aspect of the present invention is a recording medium, comprising one or more commands executable by one or more processors, wherein the one or more commands causes the one or more processors to execute operations including: generating a water image based on a digital signal containing data representing a plurality of MR signals with different echo times acquired from an imaging site including a blood vessel; and combining the water image and a signal intensity of each MR signal to generate a vascular image representing the blood vessel.

In the present invention, the water image and a signal intensity of each MR signal are combined to generate a vascular image. Therefore, even if voxel values are reduced due to swapping within the voxels of the water image, the signal intensity of each MR signal described above can compensate for the reduction in voxel values due to swapping. This allows the vascular signal loss to be reduced even when swapping occurs within a voxel.

BRIEF DESCRIPTION OF THE DRAWINGS

The present invention will be better understood by reading the following description of non-limiting embodiments with reference to the accompanying drawings, where.

DETAILED DESCRIPTION

An embodiment for carrying out the invention will be described below, but the present invention is not limited to the following embodiment.

Figure 1:
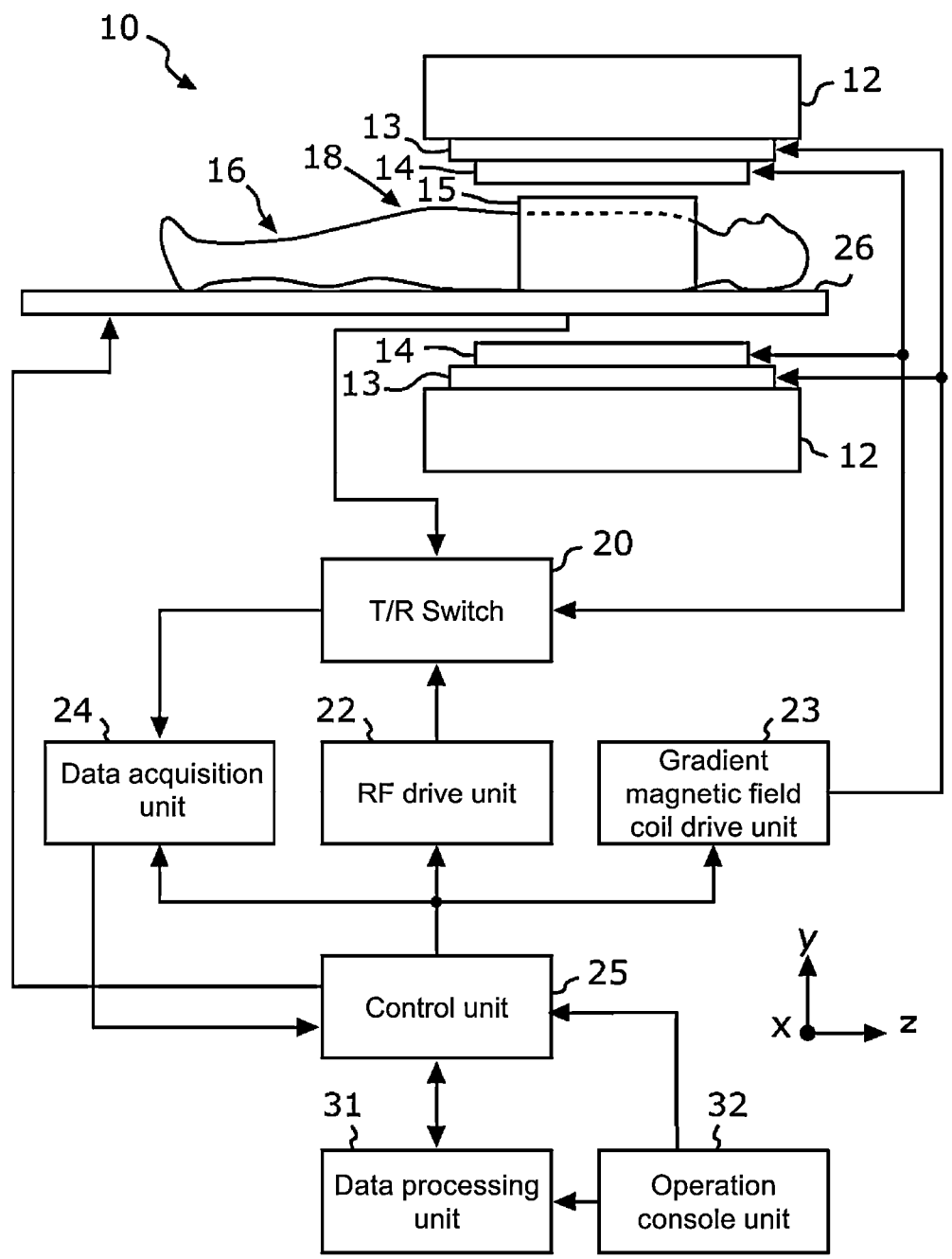
FIG. 1 is a view illustrating an MRI device of an embodiment of the present invention.

FIG. 1 is a view illustrating an MRI device of an embodiment of the present invention. The MRI device 10 has a superconducting magnet unit 12, a gradient magnetic field coil unit 13, and a body coil unit 14.

The superconducting magnet unit 12 includes, for example, an annular superconducting magnet. The magnet is provided in a toroidal vacuum container. The superconducting magnet unit 12 generates a static magnetic field B0.

Furthermore, the MRI device 10 also includes the gradient magnetic field coil unit 13. The gradient magnetic field coil unit 13 applies a gradient magnetic field to an imaging space 18. The gradient magnetic field coil unit 13 contains three gradient magnetic field coil systems. The three gradient magnetic field coil systems apply gradient magnetic fields in the frequency encoding direction, phase encoding direction, and slice selection direction in accordance with the imaging conditions. Specifically, the gradient magnetic field coil unit 13 applies gradient magnetic fields along three mutually orthogonal spatial axes (x-, y-, and z-axes).

The body coil unit 14 is an RF coil unit that can be used to apply an RF pulse to an imaging target (e.g., patient) 16 and to receive an MR signal from the imaging target 16.

The surface coil unit 15 is installed in the imaging site of the imaging target 16. The surface coil unit 15 is installed so as to surround the imaging site of the imaging target 16. The surface coil unit 15 is an RF coil unit that receives an MR signal generated in the imaging target 16. Note that the surface coil unit 15 may also be a transmitter/receiver coil that has functions of transmitting RF pulses and receiving MR signals.

Furthermore, the MRI device has a T/R switch 20, RF drive unit 22, gradient magnetic field coil drive unit 23, data acquisition unit 24, control unit 25, data processing unit 31, and operation console unit 32.

The T/R switch 20 can connect the body coil unit 14 to the data acquisition unit 24 when the body coil unit 14 operates in receive mode, and can connect the body coil unit 14 to the RF drive unit 22 when the body coil unit 14 operates in transmit mode. Furthermore, the T/R switch 20 can connect the surface coil unit 15 to the data acquisition unit 24 when the surface coil unit 15 operates in receive mode, and can connect the surface coil unit 15 to the RF drive unit 22 when the surface coil unit 15 operates in transmit mode. When the surface coil unit 15 receives MR signals and the body coil unit 14 transmits RF signals, the T/R switch 20 can be switched such that the RF drive unit 22 drives the body coil unit 14 and the MR signal received by the surface coil unit 15 is output to the data acquisition unit 24. The body coil unit 14 and surface coil unit 15 can operate in transmit-only mode, receive-only mode, or transmit-receive mode.

The RF drive unit 22 is used to drive the body coil unit 14 to form a high-frequency magnetic field in the imaging space 18 based on a control signal from the control unit 25. The RF drive unit 22 includes, for example, a gate modulator, an RF power amplifier, and an RF oscillator. In the RF drive unit 22, an RF signal received from the RF oscillator is modulated by the gate modulator. The RF signal modulated by the gate modulator can be amplified by the RF power amplifier, and output to the body coil unit 14 or the surface coil unit 15.

The gradient magnetic field coil drive unit 23 drives the gradient magnetic field coil unit 13 based on a control signal from the control unit 25, thereby generating a gradient magnetic field in the imaging space 18. The gradient magnetic field coil drive unit 23 includes three system driver circuits (not shown) corresponding to the three gradient magnetic field coil systems included in the gradient magnetic field coil unit 13.

The data acquisition unit 24 includes a pre-amplifier, phase detector, and analog/digital converter. The surface coil unit 15 outputs an analog signal corresponding to a received MR signal, and the analog signal is supplied to the pre-amplifier of the data acquisition unit 24 via the T/R switch 20. The analog signal is amplified by the pre-amplifier, the amplified analog signal is phase-detected by the phase detector, and the phase-detected analog signal is converted to a digital signal by the analog/digital converter. The digital signal obtained thereby is output to the data processing unit 31.

Furthermore, the MRI device 10 has a table. The table can be moved based on a control signal from the control unit 25 to move the imaging target 16 inside the imaging space 18.

The control unit 25 includes one or more processors and a recording medium on which a program to be executed by the one or more processors is recorded. Processors can include an electronic component that can execute a processing function, such as a digital signal processor, a field programmable gate array (FPGA), a graphics processing unit (GPU), another type of processor, or the like. The program causes the processor to execute various operations necessary to examine the imaging target 16. Recording media can include, for example, ROMs, flexible disks, hard disks, optical disks, magneto-optical disks, CD-ROMs, non-volatile memories, and the like. The control unit 25 outputs control signals to control the table, RF drive unit 22, gradient magnetic field coil drive unit 23, and data acquisition unit 24. Furthermore, the control unit 25 also controls the data processing unit 31 to acquire an MR image based on an operation signal received from the operation console unit 32.

The operation console unit 32 has an input device and display device. Input devices can include, for example, mice, joysticks, keyboards, trackballs, touch-operated screens, light pens, and other input devices. The display device, for example, displays an image on a display screen of the display device based on a control signal received from the control unit 25. Display devices can include, for example, LED (Light Emitting Diode) display units, LCD (Liquid Crystal Display) display units, and OLED (Electro-Luminescence) display units. The display device displays, for example, a two-dimensional (2D) slice image or a three-dimensional (3D) slice image of the imaging target 16 generated by the data processing unit 31. The operation console unit 32 is used by the operator, for example, to input data such as an imaging protocol or the like or to set a region where an imaging sequence is to be performed. The operation console unit 32 can communicate with the control unit 25. Data related to imaging protocols and scanning conditions are output to the control unit 25.

The data processing unit 31 includes one or more processors and a recording medium containing a program to be executed by the processor to perform prescribed data processing. Processors can include an electronic component that can execute a processing function, such as a digital signal processor, a field programmable gate array (FPGA), a graphics processing unit (GPU), another type of processor, or the like. The data processing unit 31 is connected to the control unit 25 and processes data based on a control signal received from the control unit 25. The data processing unit 31 generates an MR image based on a digital signal generated by the data acquisition unit 24.

The magnetic resonance imaging device can transmit signals between RF coils (e.g., body coil unit 14 and surface coil unit 15) and the processing system (e.g., data acquisition unit 24, control unit 25, and the like) using an RF coil array interface cable (not shown) during scanning to control the RF coils and receive MR signals by the RF coils. For example, the body coil unit 14 transmits RF signals and the surface coil unit 15 receives MR signals. The magnetic resonance imaging device can generate various MR images based on the received MR signals.

MRI devices can acquire various types of MR images, and therefore are very important in diagnosing patients. For example, if a blood vessel of a patient is to be imaged, MRA can be used to obtain a vascular image of the patient. Water-fat separation MRA by the Dixon method is known, for example, as a technique for acquiring a vascular image. Water-fat separation MRA using the Dixon method is a method of acquiring a vascular image by utilizing the property that the protons of water rotate slightly faster than the protons of fat. Water-fat separation MRA using the Dixon method is a promising technique that provides favorable fat separation, is robust to B0 and B1 inhomogeneity, and is resistant to motion artifacts. The principle of water-fat separation by the Dixon method is described below. Note that for the purpose of this description, the 2-point Dixon method, which is one of the representative techniques of water-fat separation by the Dixon method, will be described.

In the 2-point Dixon method, an in-phase signal $I_{in}$ and an out-of-phase signal $I_{out}$ are acquired. Assuming that the static magnetic field is uniform and the magnetic susceptibility is negligible, the in-phase signal $I_{in}$ and out-of-phase signal $I_{out}$ can be expressed by the following equations.

$$I_{in}=W+F \quad (1)$$

$$I_{out}=W-F \quad (2)$$

Herein, W represents a positive real value proportional to the amount of water magnetization in each voxel, and F represents a positive real value proportional to the amount of fat magnetization in each voxel.

The separated images of water magnetization and fat magnetization can be reconstructed by the following equations.

$$W=1/2(I_{in}+I_{out}) \quad (3)$$

$$F=1/2(I_{in}-I_{out}) \quad (4)$$

Furthermore, the signal intensity of $I_{in}$ and the signal intensity of $I_{out}$ can be used to express the water image and fat image in different notations.

$$Wa=1/2(|I_{in}|+\rho|I_{out}|) \quad (5)$$

$$Fa=1/2(|I_{in}|-\rho|I_{out}|) \quad (6)$$

$$\rho=+1 \text{ if } W>F$$

$$\rho=-1 \text{ if } W<F$$

Herein, Wa in equation (5) represents the water image and Fa in equation (6) represents the fat image. Furthermore, $\rho$ represents a binary code coefficient that indicates whether fat protons are dominant, or water protons are dominant in each voxel of the water image and fat image.

In the water image Wa, blood is highlighted against stationary tissue. Therefore, the water image Wa is used in clinical practice to diagnose the patient's blood flow status.

On the other hand, $\rho$ included in equation (5) representing the water image Wa is $\rho=+1$ for W>F and $\rho=-1$ for W<F. Therefore, in order to obtain a high-quality water image Wa, it is important to accurately determine whether $\rho$ is +1 or -1 for each voxel. However, the problem is that the proportions of water and fat are generally not known, making it difficult to determine $\rho$ correctly.

However, in Dixon MRA, which attempts to increase the image contrast between the blood signal and the fat-containing background signal in the water image, if there is a strong B0 inhomogeneity or magnetic susceptibility that causes a sudden phase change at the boundary between tissue and air (e.g., lungs), the correct value of $\rho$ cannot be determined and water-fat separation fails, resulting in a reduced or missing vascular signal in the water image.

Furthermore, another problem is that when a water-fat swap occurs, the vascular signal is reduced or missing in the water image, and this signal component appears as an artifact in the fat image.

Therefore, to address the aforementioned problems, an imaging method is proposed that is less likely to cause a reduction or deficiency of a vascular signal in the 2-point Dixon method. The principle of this imaging method is described below.

In one embodiment, the present technique reconstructs the water image using not only the water image Wa but also the in-phase signal intensity $|I_{in}|$ and out-of-phase signal intensity $|I_{out}|$. The following is a discussion of the composite image of the water image Wa, the in-phase signal intensity $|I_{in}|$, and the out-of-phase signal intensity $|I_{out}|$, separately for $\rho=1$ and $\rho=-1$, respectively.

When $\rho=1$ (when no swap occurs), a composite image of Wa, $|I_{in}|$ and $|I_{out}|$ can be expressed by the following equation.

$$Wns=Wa+|I_{in}|+|I_{out}|=1/2(|I_{in}|+|I_{out}|)+|I_{in}|+|I_{out}|=3/2(|I_{in}|+|I_{out}|) \quad (7)$$

Herein, Wns in equation (7) represents a composite image when no swap occurs.

In equation (7), if $Wb=1/2(|I_{in}|+|I_{out}|)$, the following equation (7)' is obtained.

$$Wns=3Wb \quad (7)'$$

When $\rho=-1$ (when a swap occurs), a composite image of Wa, $|I_{in}|$ and $|I_{out}|$ can be expressed by the following equation.

$$Ws=Wa+|I_{in}|+|I_{out}|=1/2(|I_{in}|-|I_{out}|)+|I_{in}|+|I_{out}|=3/2|I_{in}|+1/2|I_{out}| \quad (8)$$

Herein, Ws in equation (8) represents a composite image when a swap occurs.

In equation (8), if $Wb=1/2(|I_{in}|+|I_{out}|)$, the following equation (8)' is obtained.

$$Ws=Wb+|I_{in}| \quad (8)'$$

Note that the Wb in the right hand side of equations (7)' and (8)' represents the water image in an ideal situation where no swapping of water protons and fat protons occurs.

When $\rho=1$, the voxel value of each voxel in the composite image Wns of Wa, $|I_{in}|$ and $|I_{out}|$ is three times the value of Wb, as shown in equation (7)'. On the other hand, when $\rho=-1$, the voxel value of each voxel in the composite image Ws of Wa, $|I_{in}|$ and $|I_{out}|$ is the sum of Wb and $|I_{in}|$, as shown in equation (8)'.

From the aforementioned description, it can be seen that each voxel in the composite images Wns and Ws has a voxel value greater than the ideal water image Wb, where no swapping occurs. Therefore, by adding $|I_{in}|$ and $|I_{out}|$ to the voxel values of the water image Wa, it can be seen that regardless of whether water-fat swap is occurring or not, the image has larger voxel values than the ideal water image Wb where no swap is occurring. According to this method, even if a vascular defect occurs in the water image Wa due to a swap, a composite image with reduced vascular defects can be obtained because $|I_{in}|$ is added to a portion where the vascular defects occur. Focusing on this point, a vascular image is generated in accordance with the following equation, in the present embodiment.

$$C=Wa+|I_{in}|+|I_{out}| \quad (9)$$

Herein, C: Vascular image, Wa: Water image, $|I_{in}|$: Signal intensity of in-phase signal, $|I_{out}|$: Signal intensity of out-of-phase signal The following is a specific description of the procedure for generating arterial vascular images using equation (9) in the present embodiment.

Figure 2:
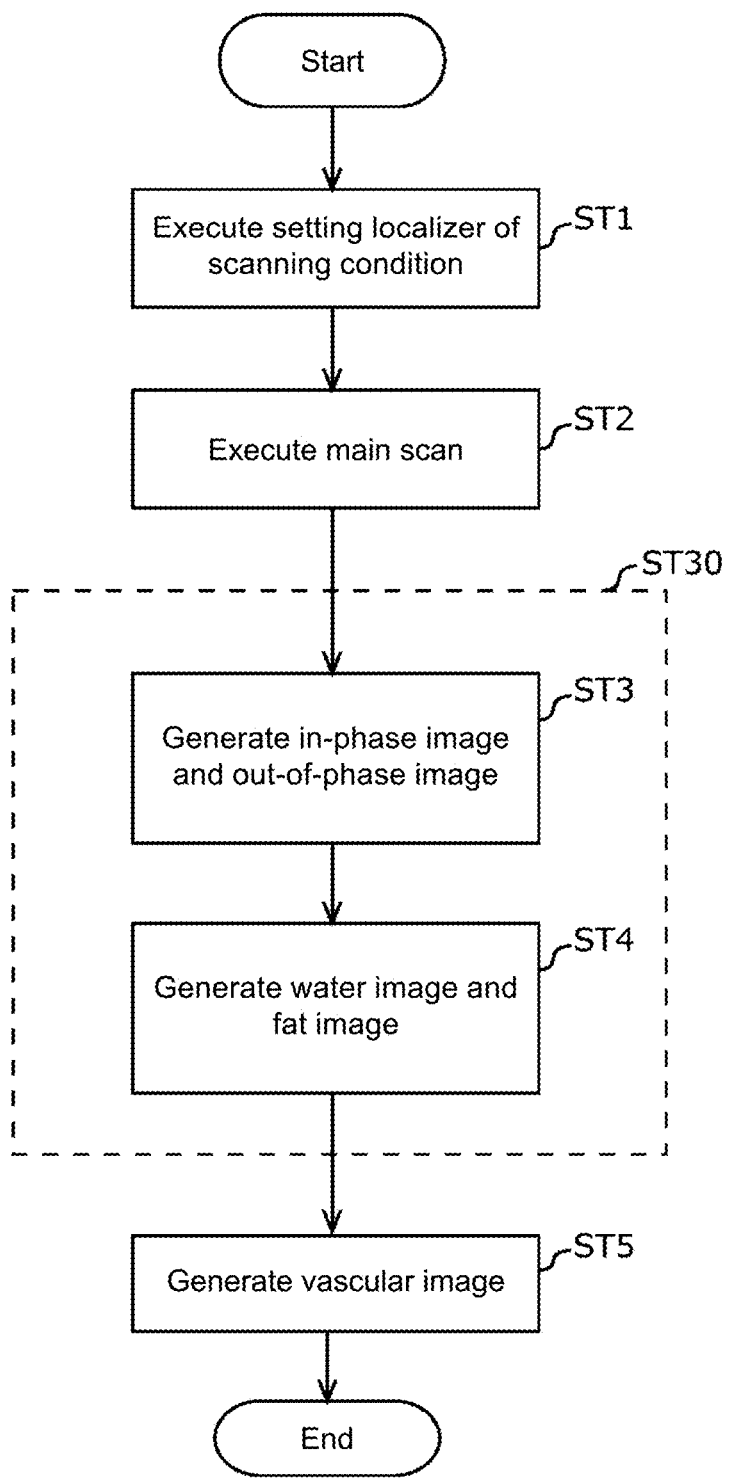
FIG. 2 is a flowchart executed to generate a vascular image by an MRI device 10 of the present embodiment.

FIG. 2 is a flowchart executed to generate a vascular image by the MRI device 10 of the present embodiment.

In step ST1, an operator sets a scanning condition. In the present embodiment, the operator sets a scanning condition for generating a vascular image using a GRE (Gradient Echo) method and the 2-point Dixon method. Scanning conditions include setting of scanning parameters, setting of slabs, and the like.

Furthermore, in step ST1, the localizer is executed. The surface coil unit 15 receives an MR signal generated by the localizer and outputs an analog signal (electrical signal) corresponding to the received MR signal. The analog signal is supplied to the data acquisition unit 24 via the T/R switch 20. The data acquisition unit 24 amplifies the analog signal, phase-detects the amplified analog signal, and converts the phase-detected analog signal to a digital signal. The processor of the data processing unit 31 executes an operation of generating a scout image based on a digital signal generated by the data acquisition unit 24. The recording medium of the data processing unit 31 stores one or more commands or one or more programs for generating a scout image. The command or program causes one or more processors to perform an operation for generating a scout image based on the digital signal.

Figure 3:
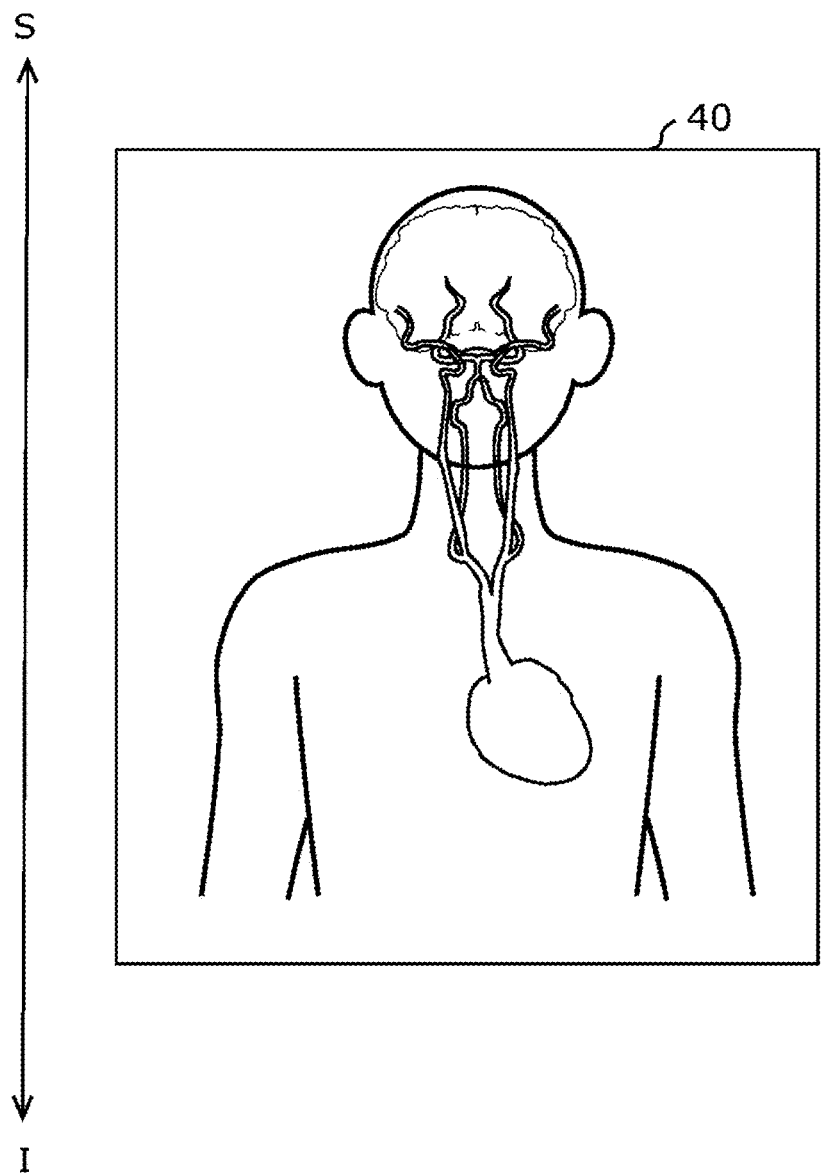
FIG. 3 is a schematic view of a scout image 40.

The scout image acquired by the localizer is used to position a slab. In the present embodiment, the depiction of blood vessels in a site that includes the patient's head and neck is considered. Therefore, the localizer acquires a scout image of the site including the patient's head and neck. The scout image acquired by the localizer is displayed on a display unit of the operation console unit 32. FIG. 3 is a schematic view of a scout image 40 displayed on a display unit. The localizer can acquire axial, sagittal, and coronal scout images. FIG. 3 illustrates an example of a coronal scout image 40 on the display unit. Furthermore, FIG. 3 also illustrates a SI (superior-inferior) direction, which represents a craniocaudal direction.

Figure 4:
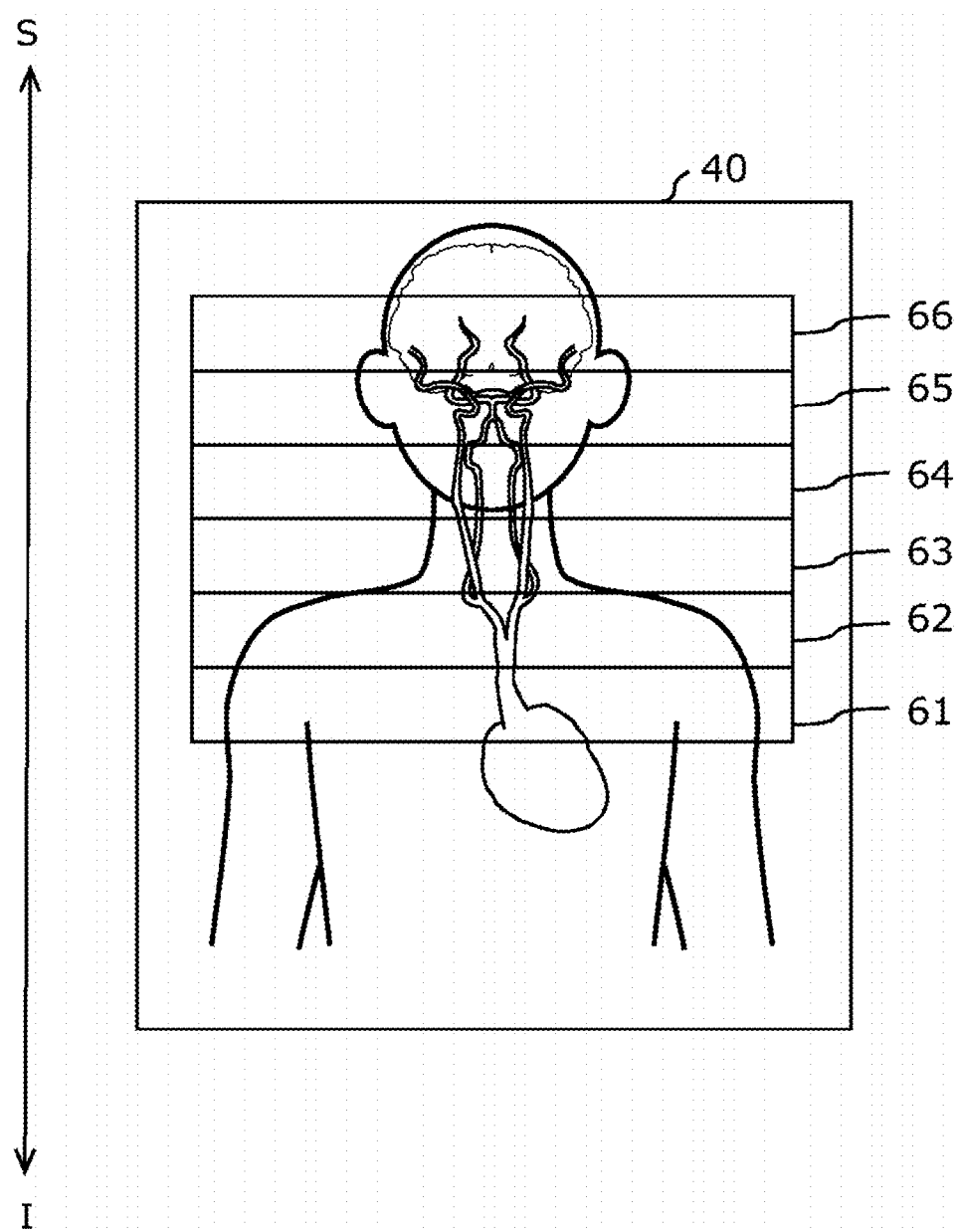
FIG. 4 is an explanatory diagram of a slab set by an operator.

After running the localizer, the operator sets a slab on the scout image 40 (see FIG. 4).

FIG. 4 is an explanatory diagram of the slab set by the operator. The operator operates the input device of the operation console unit 32 to input an operation signal to set the slab at the imaging site. The display device of the operation console unit 32 displays the slab on the scout image 40. The processor of the operation console unit 32, the data processing unit 31, and/or the control unit 25 can process the operation signal input from the input device of the operation console unit 32, and can display the slab on the display device of the operation console unit 32. The recording medium of the operation console unit 32, the data processing unit 31, and/or the control unit 25 store one or more commands or one or more programs for displaying the slab based on the operation signal. The command or program causes one or more processors to perform an operation for generating a slab based on the operation signal from the input device.

In the present embodiment, an example of setting six slabs 61 to 66 is shown, but considering the range of the imaging site, one to five slabs may be set, or seven or more slabs may be set. Note that the six mutually adjacent slabs 61 to 66 can be set to overlap in order to reduce image quality degradation at a boundary portion of the adjacent slabs. Once the slabs 61 to 66 are set, the process proceeds to step ST2.

In step ST2, a main scan of a specimen is executed in accordance with the set protocol.

Figure 5:
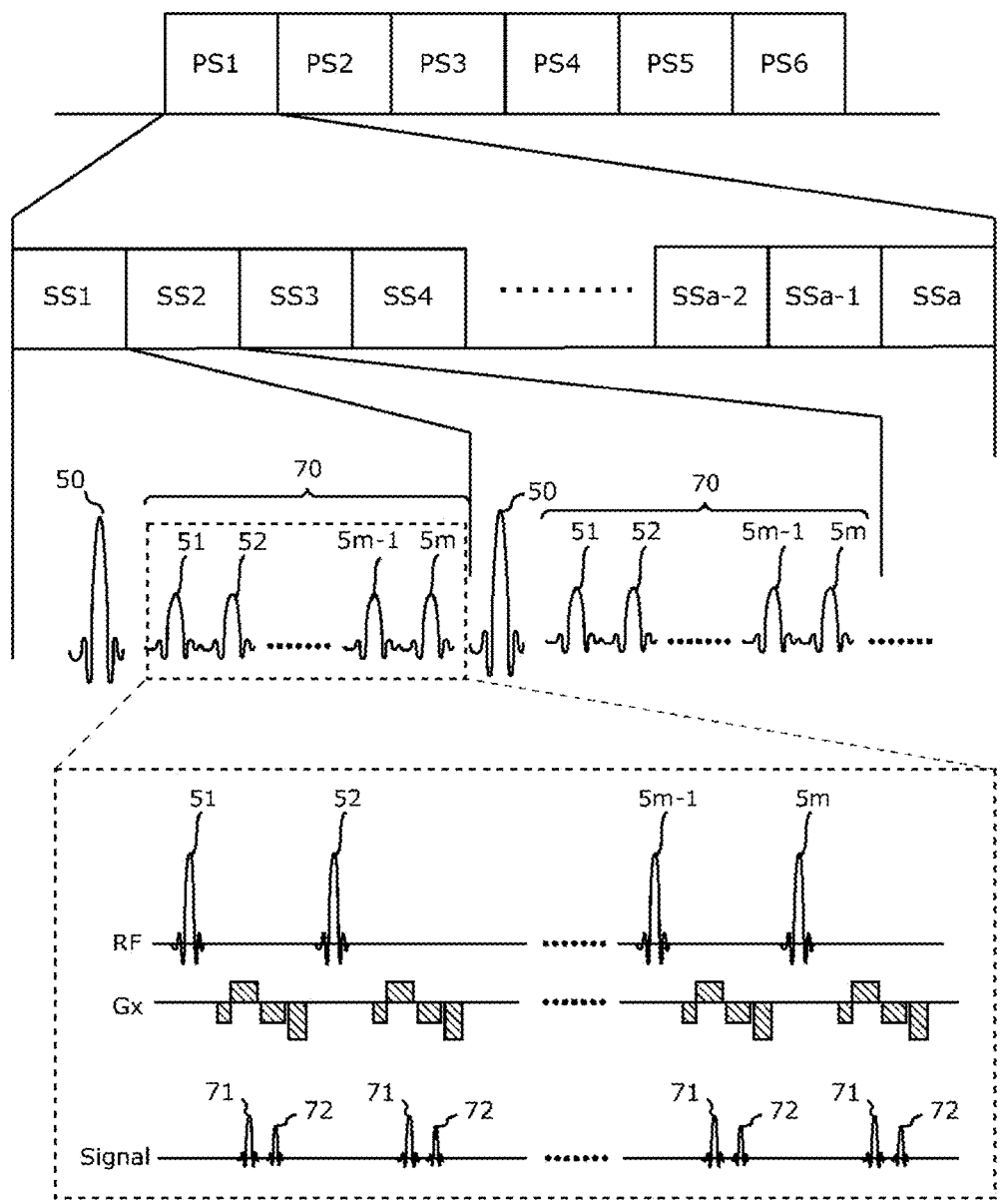
FIG. 5 is an explanatory diagram of a pulse sequence used to scan a specimen.

FIG. 5 is an explanatory diagram of a pulse sequence used to scan a specimen. When scanning the specimen, a pulse sequence PSj (j=1 to 6) is executed. The pulse sequence PSj is a pulse sequence for collecting data using the GRE and 2-point Dixon methods. In the present embodiment, j=1 to 6, i.e., six pulse sequences PS1 to PS6 are executed, but the number of times the pulse sequence PSj is executed may be five or less (e.g. 1 time) or 7 or more times. The pulse sequences PS1 through PS6 are sequences executed for collecting data from the slabs 61 to 66, respectively.

FIG. 5 shows a specific configuration of the pulse sequence PS1 as a representative of the pulse sequences PS1 to PS6. The pulse sequences PS1 to PS6 are described below.

When the execution of the main scan is started, the pulse sequence PS1 is first performed to collect data from the slab 61 (see FIG. 4).

The pulse sequence PS1 includes a plurality of sub-sequences SSr (r=1 to a). Focusing on a sub-sequence SSr with r=1, i.e., a sub-sequence SS1, sub-sequence SS1 has an SAT (saturation) pulse 50.

Figure 6:
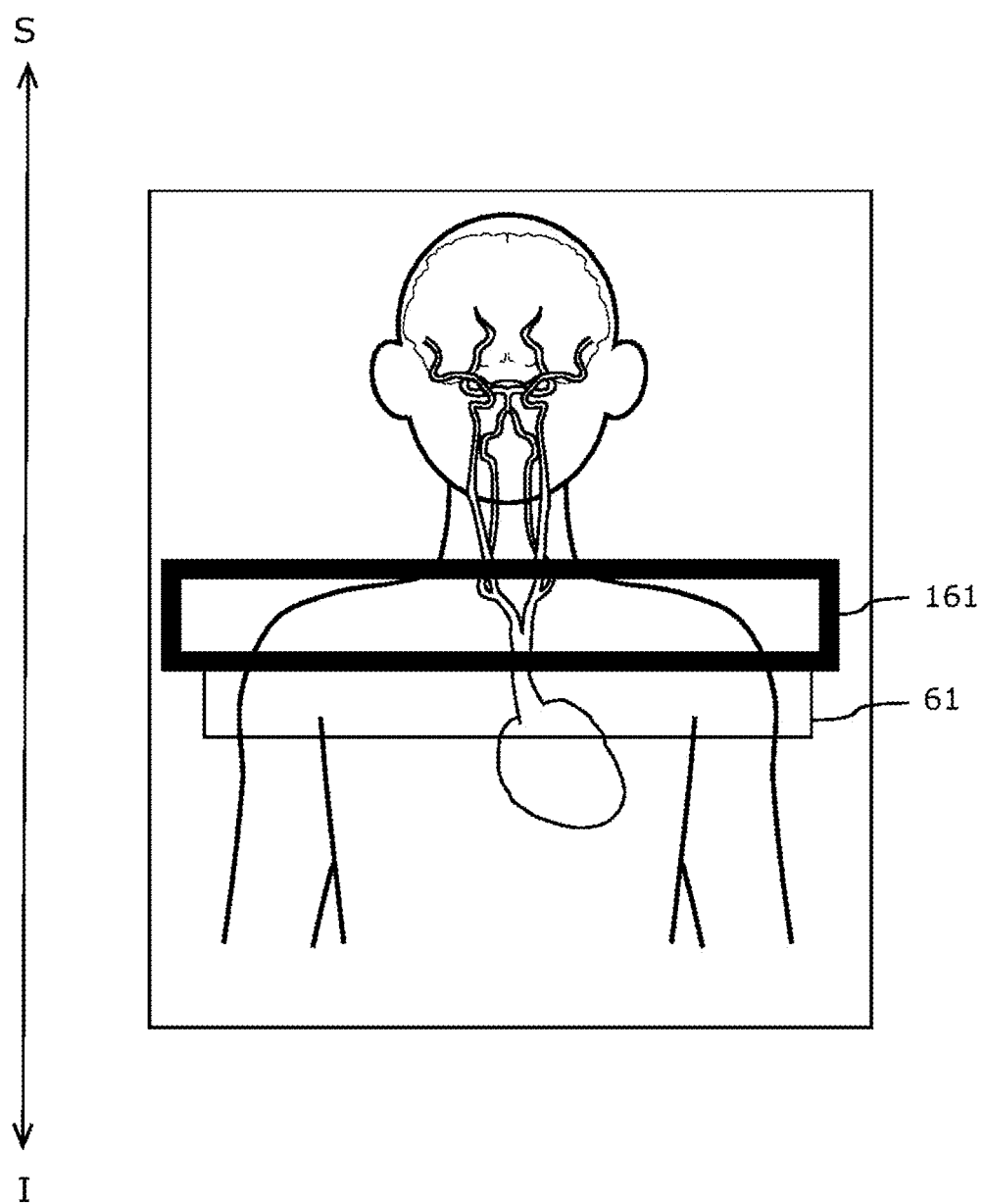
FIG. 6 is an explanatory diagram of an SAT pulse 50.

FIG. 6 is an explanatory diagram of the SAT pulse 50. The SAT pulse 50 is a pulse for eliminating the magnetization of venous blood flowing within a region 161 adjacent to the slab 61. The processor of the control unit 25 and/or data processing unit 31 executes an operation of positioning the region 161 based on data representing the position of the slab 61 set by the operator. The recording medium of the control unit 25 and/or data processing unit 31 stores one or more commands or one or more programs for positioning the region 161, based on data representing the position of the slab. The command or program causes one or more processors to perform an operation for positioning the region 161. Specifically, the processor positions the region 161 so as to be adjacent to the slab 61 on the S (Superior) side in the SI direction with respect to the slab 61. The SAT pulse 50 can demagnetize venous blood flowing in the region 161, and therefore, a signal of venous blood in the slab 61 can be suppressed even if venous blood flows from the region 161 into the slab 61.

The width of the region 161 can be determined based on the width of the slab 61, the flow rate of the venous blood, and the like. Note that the region 161 can be positioned such that a portion of the region 161 overlaps with the slab 61. Furthermore, the region 161 can be positioned such that a certain gap is provided between the region 161 and the slab 61.

Returning to FIG. 5, the description is continued. The sub-sequence SS1 includes a data collection sequence part 70 for collecting MR signals with different echo times by the 2-point Dixon method after the SAT pulse 50. The data collection sequence part 70 includes m-number of $\alpha°$ pulses $5u$ (u=1, 2, ... m-1, m). The m-number of $\alpha°$ pulses 51, 52, ... 5m-1, 5m are pulses applied after the SAT pulse 50. $\alpha°$ can be an angle smaller than 90°, for example, between 20° and 70°, but can also be set to an angle outside the range of 20° to 70°.

Furthermore, the data collection sequence part 70 also includes gradient magnetic fields Gx, Gy, and Gz. In FIG. 5, the gradient magnetic field Gx is shown. The gradient magnetic fields Gy and Gz are omitted from the drawings.

After the SAT pulse 50 is applied, the $\alpha°$ pulse 51 and a gradient magnetic field are applied, and an out-of-phase signal 71 and in-phase signal 72 are generated in sequence. The echo time TE of the out-of-phase signal 71 is approximately 2.3 msec, and the echo time TE of the in-phase signal 72 is approximately 4.6 msec.

After a certain amount of time has elapsed from the α° pulse 51, the subsequent α° pulse 52 (and gradient magnetic field) is applied, and the subsequent out-of-phase signal 71 and in-phase signal 72 are collected.

Hereinafter, in the same manner, an α° pulse 5u and a gradient magnetic field are applied, and each time an α° pulse is applied, an out-of-phase signal 71 and in-phase signal 72 can be collected from the slab 61. After the mth α° pulse 5m is applied, the out-of-phase signal 71 and in-phase signal 72 are collected. Thereby, the sub-sequence SS1 can be executed to collect out-of-phase signals and in-phase signals.

Note that the number m of α° pulses in the sub-sequence SS1 can be determined by considering the time during which the venous blood suppression effect of the SAT pulse 50 is maintained and the like. For example, m=200 can be set.

After the sub-sequence SS1 is executed, the subsequent sub-sequence SS2 is executed.

The sub-sequence SS2 is the same as the sub-sequence SS1, except that the magnetic field intensity of the phase-encoded gradient magnetic field is different.

Therefore, even in the sub-sequence SS2, the SAT pulse 50 is applied first, followed by m-number of α° pulses 5u (u=1 to m), and the out-of-phase signal 71 and in-phase signal 72 are collected.

The subsequent sub-sequence SSr is repeatedly executed in the same manner. In the present embodiment, the sub-sequence SSr is repeated a-number of times. By executing the sub-sequences SS1 to SSa, a series of MR signals required to reconstruct an image of the slab 61 can be collected. The value of a can be, for example, a=10.

Figure 7:
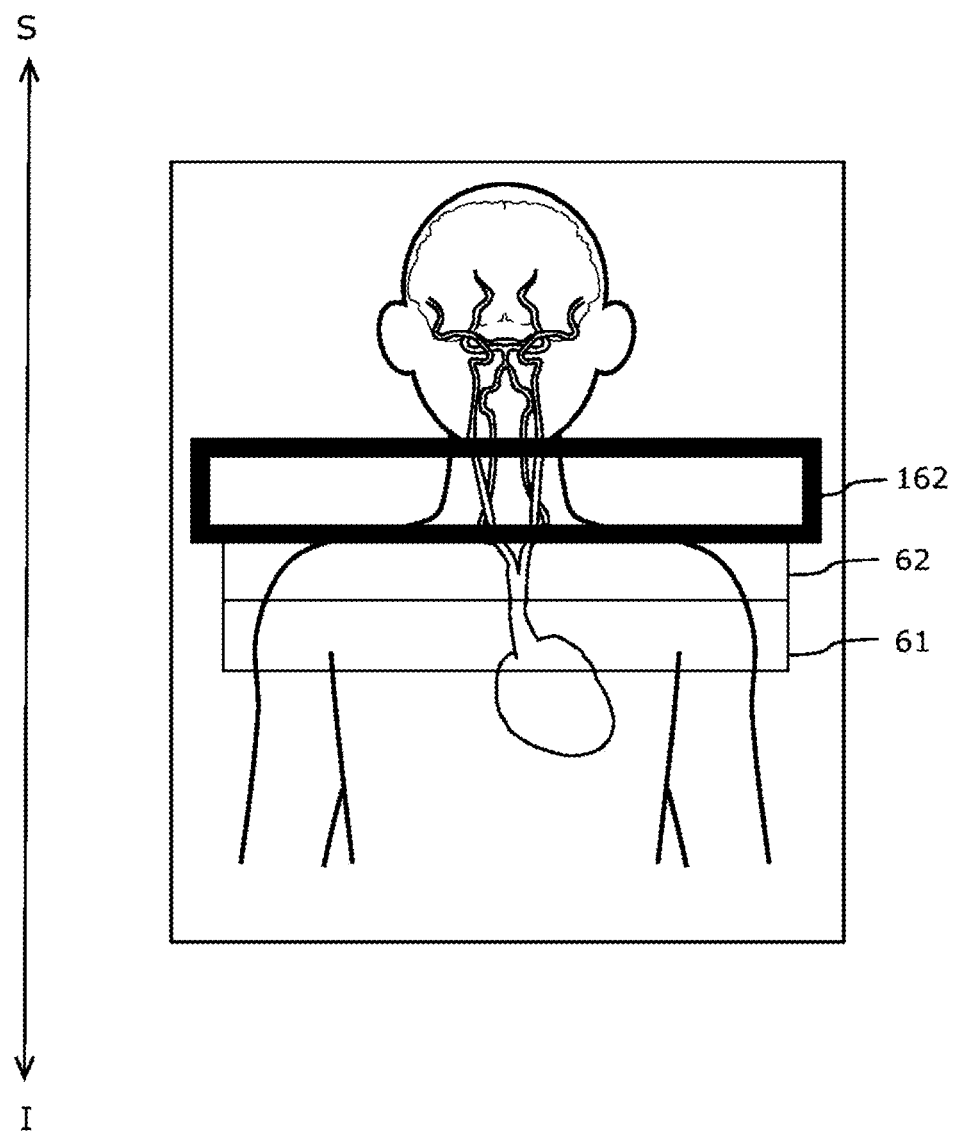
FIG. 7 is an explanatory diagram of a pulse sequence PS2.

Once data collection for the slab 61 is complete, a pulse sequence PS2 for collecting data for the subsequent slab 62 is executed. The pulse sequence PS2, similarly to pulse sequence PS1, has the sub-sequence SSr (r=1 to a). However, the pulse sequence PS2, as illustrated in FIG. 7, differs from the pulse sequence PS1 in that the α° pulse is designed to excite the slab 62 and the SAT pulse is designed to excite a region 162 adjacent to the slab 62. Therefore, the pulse sequence PS2 can be executed to collect data necessary for image reconstruction of the slab 62 while suppressing venous blood.

In the same manner below, pulse sequences PS3 to PS6 for collecting data from the remaining slabs 63 to 66 are executed in sequence.

The pulse sequences PS3 to PS6, similarly to pulse sequence PS1, have a-number of sub-sequences SS1 to SSa. However, the α° and SAT pulses are designed to be different from the pulse sequence PS1. Specifically, the pulse sequences PS3 to PS6 are designed as follows.

The pulse sequence PS3 is designed such that the α° pulse excites the slab 63 and the SAT pulse excites a region adjacent to the slab 63 on the S side in the SI direction with respect to the slab 63.

The pulse sequence PS4 is designed such that the α° pulse excites the slab 64 and the SAT pulse excites a region adjacent to the slab 64 on the S side in the SI direction with respect to the slab 64.

The pulse sequence PS5 is designed such that the α° pulse excites the slab 65 and the SAT pulse excites a region adjacent to the slab 65 on the S side in the SI direction with respect to the slab 65.

The pulse sequence PS6 is designed such that the α° pulse excites the slab 66 and the SAT pulse excites a region adjacent to the slab 66 on the S side in the SI direction with respect to the slab 66.

Therefore, the pulse sequences PS1 to PS6 can be executed to collect data necessary for image reconstruction from the slabs 61 to 66.

The control unit 25 (see FIG. 1) controls the RF drive unit 22 and gradient magnetic field coil drive unit 23 such that the aforementioned pulse sequences PS1 to PS6 are executed. In order to control the RF drive unit 22 and the gradient magnetic field coil drive unit 23, one or more commands or one or more programs are stored in the recording medium of the control unit 25. The command or program causes one or more processors to execute an operation to generate control signals for controlling the RF drive unit 22 and gradient magnetic field coil drive unit 23 such that the aforementioned pulse sequences PS1 to PS6 are executed.

The out-of-phase signals 71 and in-phase signals 72 generated by executing the pulse sequences PS1 to PS6 are received by the surface coil unit 15. The surface coil unit 15 outputs analog signals corresponding to the received out-of-phase signal 71 and in-phase signal 72 to the data acquisition unit 24.

The data acquisition unit 24 generates a digital signal representing the out-of-phase signal 71 and in-phase signal 72 based on the analog signal from the surface coil unit 15. The digital signal is output to the control unit 25. After the digital signal is generated, the process proceeds to step ST30.

In step ST30, the processor of the control unit 25 and/or the data processing unit 31 generates water and fat images based on the digital signal from data acquisition unit 24. Step ST30 includes steps ST3 and ST4. Steps ST3 and ST4 are described below.

In step ST3, the processor of the control unit 25 and/or the data processing unit 31 executes a process of generating an in-phase image and out-of-phase image based on the digital signal from data acquisition unit 24. The recording medium of the control unit 25 and/or data processing unit 31 stores one or more commands or one or more programs for generating the in-phase image and out-of-phase image. The command or program causes one or more processors to perform an operation for generating an in-phase image and out-of-phase image. After the in-phase image and out-of-phase image are generated, the process proceeds to step ST4.

In step ST4, the processor of the control unit 25 and/or the data processing unit 31 executes an operation of applying a water-fat separation on to the in-phase and out-of-phase images generated in step ST3 and generating the water image Wa and fat image Fa. The recording medium of the control unit 25 and/or data processing unit 31 stores one or more commands or one or more programs for generating the water image Wa and fat image Fa. The command or program causes one or more processors to perform an operation for generating the water image Wa and fat image Fa. The water image Wa can be generated in accordance with equation (5) and the fat image Fa can be generated in accordance with equation (6). Note that the value of ρ in the right hand side of equations (5) and (6) is ρ=1 when the water protons are dominant, and ρ=−1 if the fat protons are dominant. In the water-fat separation technique, for example, a B0 map can be used. After the water image Wa and fat image Fa are generated, the process proceeds to step ST5.

In step ST5, the processor of the control unit 25 and/or data processing unit 31 combines the water image Wa, in-phase signal intensity $|I_{in}|$, and out-of-phase signal intensity $|I_{out}|$ to generate a vascular image C. The recording medium of the control unit 25 and/or data processing unit 31 stores one or more commands or one or more programs for generating the vascular image C. The command or program causes one or more processors to perform an operation for generating the vascular image C.

The vascular image C can be obtained using equation (9) described earlier. The value of the in-phase signal intensity $|I_{in}|$ can be the voxel value of the in-phase image generated in step ST3, and the out-of-phase signal intensity $|I_{out}|$ can be the voxel value of the out-of-phase image generated in step ST3. Once the vascular image C is generated in this manner, the flow shown in FIG. 2 ends.

In the present embodiment, the vascular image C is a composite image of Wa, $|I_{in}|$ and $|I_{out}|$. As described earlier, when no swap has occurred, the vascular image C can be determined using equation (9) to obtain a vascular image C with three times the voxel value of the ideal water image Wb in which no swap has occurred, that is, a vascular image with a voxel value of 3Wb. On the other hand, even if a swap occurs, by obtaining the vascular image C using equation (9), the addition of $|I_{in}|$ to the ideal water image Wb, in which no swap has occurred, results in a vascular image with reduced vascular defects. Thereafter, the vascular image C with reduced vascular defects can be obtained regardless of whether or not a swap between water protons and fat protons occurs.

Furthermore, in the present embodiment, whether $\rho=1$ (when no swap occurs) or $\rho=-1$ (when a swap occurs), the vascular image C can have a value at least $|I_{in}|$ greater than the ideal water image Wb, where no swap occurs (see equations (7)' and (8)'). Therefore, even if the true value of $\rho$ is incorrectly determined to be $\rho=-1$ for a voxel where $\rho=1$, the vascular image C with a value that is greater than the ideal water image Wb by $|I_{in}|$ can be obtained. Thus, a vascular image with reduced vessel loss can be obtained. Therefore, the present embodiment can provide a robust vascular image generation method that is less susceptible to the quality of the accuracy of the $\rho$ determination.

Note that although the present embodiment describes an example of generating an arterial vascular image, the present invention can also be applied to generating a venous vascular image.

Note that in order to make the principle of the present invention easier to understand, the present embodiment discusses an example in which each pulse sequence PSj (j=1 to 6) includes a sub-sequence SSr (r=1 to a) that includes 50 SAT pulses and $5u$ $\alpha°$ pulses (u=1 to m) (see FIG. 5). However, pulse sequences executed in the present invention are not limited to the aforementioned examples. A basic configuration of a pulse sequence of another embodiment of the present invention is described below.

Figure 8:
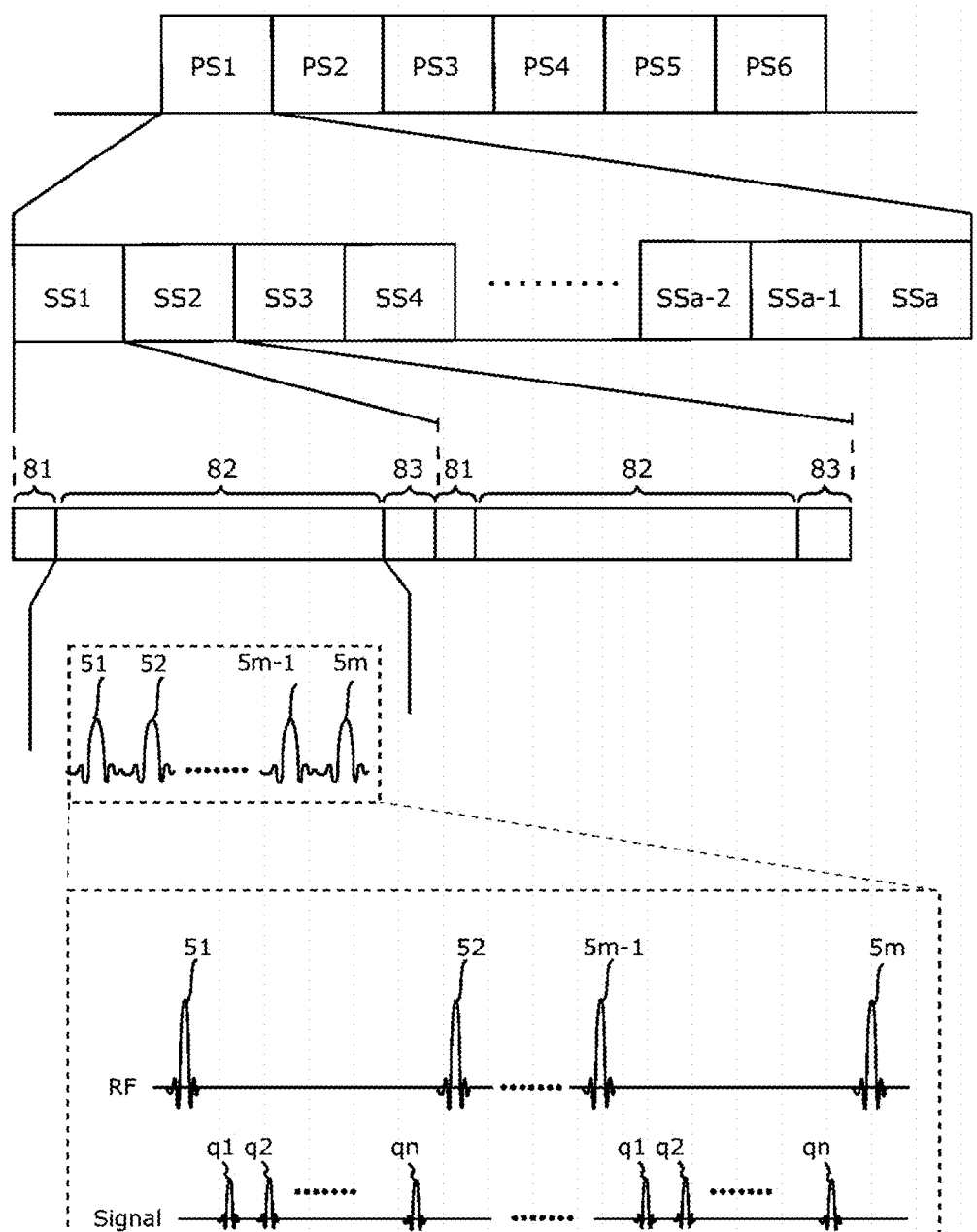
FIG. 8 is an explanatory diagram of a basic configuration of a pulse sequence of another embodiment of the present invention.

FIG. 8 is an explanatory diagram of a basic configuration of a pulse sequence of another embodiment of the present invention. Each pulse sequence PSj includes an a-number of sub-sequences SSr (r=1 to a). Each sub-sequence SSr includes a preparation pulse part 81, a data collection sequence part 82 using the Dixon method, and a waiting time 83.

The preparation pulse part 81 includes one or more preparation pulses applied to enhance the contrast of a particular tissue against the background, to suppress the signal of background tissue, or to suppress an artifact. Examples of preparation pulses include SAT pulses, DE (Driven Equilibrium) pulses (e.g., T2prep), IR (Inversion Recovery) pulses, DIR (Double Inversion Recovery) pulses, navigator pulses, fat suppression pulses (e.g., Fat Sat), and magnetization transfer enhancement (MT) pulses. The previously described embodiment (see FIG. 5) is equivalent to the example in which the preparation pulse part 81 includes an SAT pulse 50.

The data collection sequence part 82 includes a pulse for collecting data using the multi-point Dixon method. FIG. 8 is an example where an n-point Dixon method is used, in which n-number of MR signals qi (i=1 to n) with different echo times TE between adjacent $\alpha°$ pulses are collected between adjacent $\alpha°$ pulses. Therefore, the surface coil unit 15 receives n-number of MR signals q1, q2, . . . , qn with different echo times TE. For example, if n=3, i.e., data is collected using the 3-point Dixon method, and the surface coil unit 15 receives MR signals q1, q2, and q3. Furthermore, if n=2, i.e., data is collected using the 2-point Dixon method, and the surface coil unit 15 receives MR signals q1 and q2. The previously described embodiment (see FIG. 5) corresponds to an example in which the 2-point Dixon method is used to collect MR signals q1 and q2 (i.e., out-of-phase signal 71 and in-phase signal 72).

The waiting time 83 is the time provided from the end of the data collection sequence part 82 of the sub-sequence SSr to the start of the execution of the subsequent sub-sequence SSr+1 to recover the longitudinal magnetization of spin. The waiting time 83 can be set to zero.

By repeating the execution of the aforementioned sub-sequence SSr a-number of times, data necessary to reconstruct a 3D image of one slab can be collected.

The control unit 25 generates a control signal for controlling the gradient magnetic field coil drive unit 23 and the RF drive unit 22 such that the pulse sequence PSj is repeatedly executed to collect an MR signal from each slab repeatedly. Therefore, the data necessary for image reconstruction of each slab can be collected.

The vascular image generated based on data obtained by the pulse sequence PSj shown in FIG. 8 can be expressed by the following equation.

$$C = \{a_0 * Wa + a_1 * |I_{q1}| + a_2 * |I_{q2}| + a_3 * |I_{q3}| + \ldots + a_n * |I_{qn}|\}/A \qquad (10)$$

However, $A = a_0 + a_1 + a_2 + a_3 \ldots + a_n$

Herein, C: Vascular image; Wa: Water image; $|I_{qi}|$(i=1 to n): Signal intensity of the i-th generated MR signal of the n-number of MR signals q1, q2, . . . qn; ai(i=0 to n): Coefficient.

The vascular image C is an image obtained by combining the water image Wa and the signal intensity $|I_{qi}|$ of each MR signal. A is the additive value of the coefficients ai (a0 to an). The value of the coefficient ai can be determined based on the T1 value, T2 value, and the like of background tissue to be suppressed.

The previously described embodiment (see FIG. 5) corresponds to the examples of $a_0=a_1=a_2=1$, $a_3$ to $a_n=0$, $|I_{q1}|=|I_{out}|$ and $|I_{q2}|=|I_{in}|$ in equation (10).

If the vascular image C is generated using equation (10), the recording medium of the control unit 25 and/or data processing unit 31 stores one or more commands or one or more programs for generating the vascular image C using equation (10). The command or program causes one or more processors to perform an operation for generating the vascular image C using equation (10). The processor of the control unit 25 and/or data processing unit 31 can execute one or more commands or one or more programs to perform the operation of generating the vascular image C using equation (10).

Next, to clarify the effect of the present embodiment, a water image and a vascular image were generated, and these images were compared. The results of the image comparison are described below.

Figure 9:
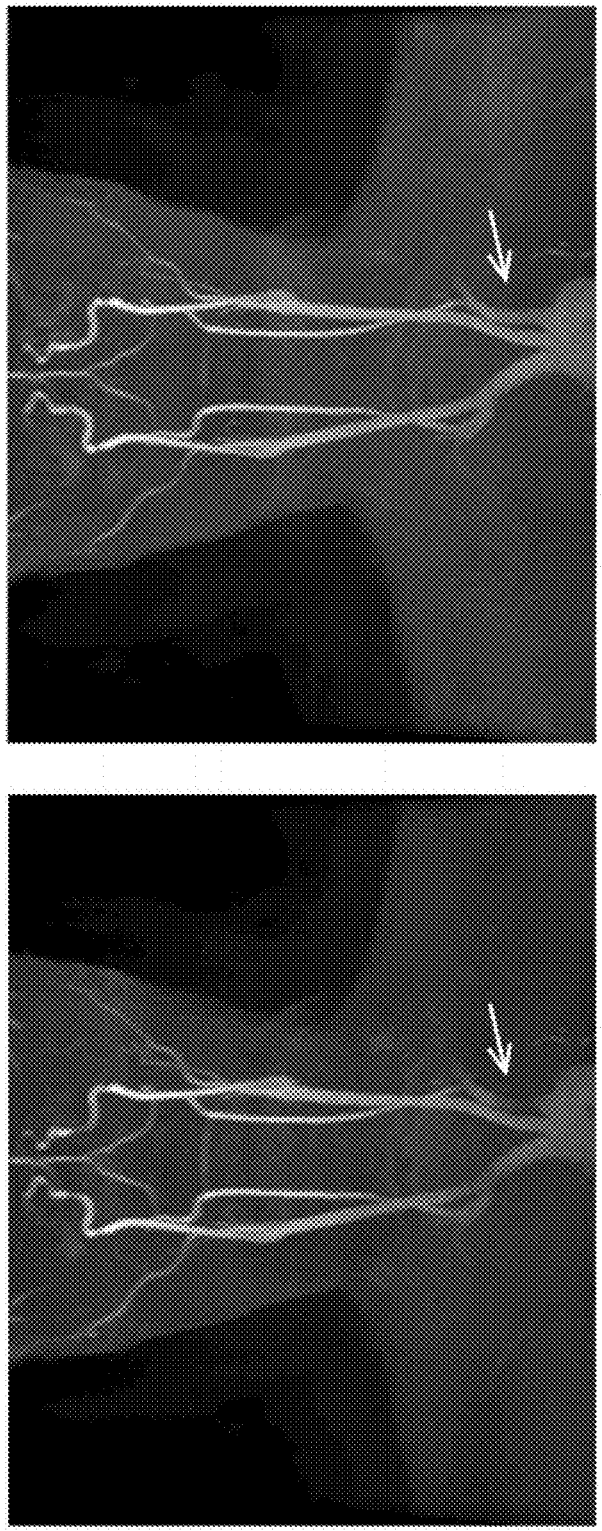
FIG. 9 is a diagram showing an example of a water image and an example of a vascular image.

FIG. 9 is a diagram showing an example of a water image and an example of a vascular image. The water image shows that the blood vessel portion near the heart is missing. On the other hand, the vascular image shows that the deficiency in the vascular portion near the heart is improved.

The invention claimed is:

1. A magnetic resonance imaging device that receives a plurality of MR signals with different echo times from an imaging site including a blood vessel, comprising:
    one or a plurality of processors that process a digital signal including data representing the plurality of MR signals;
    the one or plurality of processors executing an operation including:
    generating a water image based on the digital signal; and
    combining the water image, an out-of-phase signal intensity, and an in-phase signal intensity to generate a vascular image representing the blood vessel.

2. The magnetic resonance imaging device according to claim 1, comprising:
    a first driving part that drives a first RF coil unit;
    a second driving part that drives a gradient magnetic field coil unit; and
    a control unit that controls the first driving part and the second driving part such that a pulse sequence for generating the plurality of MR signals with different echo times from the imaging sites is executed;
    wherein the pulse sequence includes a plurality of sub-sequences, and
    each of the plurality of sub-sequences includes a preparation pulse part including one or more preparation pulses, and a data collection sequence part for collecting the plurality of MR signals by a multi-point Dixon method.

3. The magnetic resonance imaging device according to claim 2, wherein each of the plurality of sub-sequences includes a waiting time for allowing a longitudinal magnetization of spin to recover, between the data collection sequence part of the sub-sequence and a subsequent sub-sequence.

4. The magnetic resonance imaging device according to claim 2, wherein the preparation pulse part includes a preparation pulse that suppresses a background tissue signal.

5. The magnetic resonance imaging device according to claim 4, wherein the vascular image is an arterial vascular image, and
    the preparation pulse is a saturation (SAT) pulse for demagnetizing of venous blood flowing through a region adjacent to a slab.

6. The magnetic resonance imaging device according to claim 5, further comprising an input device that is operated by an operator to input an operation signal for setting the slab to the imaging site, wherein
    the processor executes an operation of positioning the region.

7. The magnetic resonance imaging device according to claim 6, wherein the processor executes an operation of positioning the region so as to be adjacent to the slab on a superior side in a superior-inferior direction with respect to the slab.

8. The magnetic resonance imaging device according to claim 7, wherein an operation signal for setting a plurality of slabs to the imaging site is input from the input device, the processor executes an operation of positioning the region with respect to each of the plurality of slabs, and
    the control unit generates a control signal for controlling the first driving part and the second driving part such that the pulse sequence is repeatedly executed to acquire an MR signal from the plurality of slabs.

9. The magnetic resonance imaging device according to claim 2, wherein the multi-point Dixon method is a two-point Dixon method.

10. The magnetic resonance imaging device according to claim 2, comprising:
    a second RF coil unit that receives the plurality of MR signals with different echo times and outputs an analog signal corresponding to the received MR signals; and
    a data acquisition unit that generates a digital signal containing data representing the plurality of MR signals based on the analog signal.

11. The magnetic resonance imaging device according to claim 1,
    wherein the one or plurality of processors executes an operation of generating the vascular image based on the following:

$$C = \{a_0 * Wa + a_1 * |I_{q1}| + a_2 * |I_{q2}| + a_3 * |I_{q3}| + \ldots + a_n * |I_{qn}|\}/A$$

where, $A = a_0 + a_1 + a_2 + a_3 \ldots + a_n$
$C$: The vascular image
$Wa$: The water image
$|I_{qi}|$ (i=1 to n): Signal intensity of the i-th generated MR signal of the plurality of MR signals; and
$a_i$ (i=0 to n): Coefficient.

12. The magnetic resonance imaging device according to claim 1, wherein generating a water image based on the digital signal includes:
    generating an out-of-phase image and in-phase image based on the digital signal; and
    generating the water image based on the out-of-phase image and in-phase image.

13. A vascular image generation method, comprising:
    receiving a plurality of MR signals with different echo times from an imaging site including a blood vessel;
    generating a water image based on a digital signal containing data representing the plurality of MR signals; and
    combining the water image, an out-of-phase signal intensity, and an in-phase signal intensity to generate a vascular image representing the blood vessel.

14. The vascular image generation method of claim 13, further comprising:
    executing a pulse sequence for generating the plurality of MR signals with different echo times from the imaging sites;
    wherein the pulse sequence includes a plurality of sub-sequences, and
    each of the plurality of sub-sequences includes a preparation pulse part including one or more preparation pulses, and a data collection sequence part for collecting the plurality of MR signals by a multi-point Dixon method.

15. The vascular image generation method of claim 13, further comprising generating the vascular image based on the following:

$$C = \{a_0 * Wa + a_1 * |I_{q1}| + a_2 * |I_{q2}| + a_3 * |I_{q3}| + \ldots + a_n * |I_{qn}|\}/A$$

where, $A=a_0+a_1+a_2+a_3 \ldots +a_n$

C: The vascular image

Wa: The water image $|I_{qi}|$(i=1 to n): Signal intensity of the i-th generated MR signal of the plurality of MR signals; and ai(i=0 to n): Coefficient.

16. The vascular image generation method of claim 13, wherein generating the water image based on the digital signal comprises:

generating an out-of-phase image and in-phase image based on the digital signal; and generating the water image based on the out-of-phase image and in-phase image.

17. A non-transitory computer-readable storage medium, comprising one or more commands executable by one or more processors, wherein the one or more commands cause the one or more processors to execute operations including:

generating a water image based on a digital signal containing data representing a plurality of MR signals with different echo times acquired from an imaging site including a blood vessel; and combining the water image, an out-of-phase signal intensity, and an in-phase signal intensity to generate a vascular image representing the blood vessel.

18. The non-transitory computer-readable storage medium of claim 17, wherein the one or more commands cause the one or more processors to execute a pulse sequence for generating the plurality of MR signals with different echo times from the imaging sites;

wherein the pulse sequence includes a plurality of sub-sequences, and each of the plurality of sub-sequences includes a preparation pulse part including one or more preparation pulses, and a data collection sequence part for collecting the plurality of MR signals by a multi-point Dixon method.

19. The non-transitory computer-readable storage medium of claim 17, wherein the one or more commands cause the one or more processors to execute operations including generating the vascular image based on the following:

$$C=\{a_0*Wa+a_1*|I_{q1}|+a_2*|I_{q2}|+a_3*|I_{q3}|+ \ldots +a_n*|I_{qn}|\}/A$$

where, $A=a_0+a_1+a_2+a_3 \ldots +a_n$

C: The vascular image

Wa: The water image $|I_{qi}|$(i=1 to n): Signal intensity of the i-th generated MR signal of the plurality of MR signals; and ai(i=0 to n): Coefficient.

20. The non-transitory computer-readable storage medium of claim 17, wherein generating the water image based on the digital signal comprises:

generating an out-of-phase image and in-phase image based on the digital signal; and generating the water image based on the out-of-phase image and in-phase image.

* * * * *